US009804295B2

(12) United States Patent
Winterton et al.

(10) Patent No.: US 9,804,295 B2
(45) Date of Patent: Oct. 31, 2017

(54) OPHTHALMIC DEVICES FOR SUSTAINED DELIVERY OF ACTIVE COMPOUNDS

(75) Inventors: Lynn Cook Winterton, Alpharetta, GA (US); John Martin Lally, Lilburn, GA (US)

(73) Assignee: Novartis AG, Basel (CH)

( * ) Notice: Subject to any disclaimer, the term of this patent is extended or adjusted under 35 U.S.C. 154(b) by 2263 days.

(21) Appl. No.: 11/416,260

(22) Filed: May 2, 2006

(65) Prior Publication Data
US 2006/0251696 A1 Nov. 9, 2006

(51) Int. Cl.
*G02B 1/04* (2006.01)
*A61K 9/00* (2006.01)
*B29D 11/00* (2006.01)

(52) U.S. Cl.
CPC ............ *G02B 1/043* (2013.01); *A61K 9/0051* (2013.01); *B29D 11/00038* (2013.01); *B29D 11/00865* (2013.01)

(58) Field of Classification Search
None
See application file for complete search history.

(56) References Cited

U.S. PATENT DOCUMENTS

| | | | |
|---|---|---|---|
| 3,408,429 A | 10/1968 | Wichterle | 264/1 |
| 4,312,575 A | 1/1982 | Peyman et al. | 351/160 |
| 4,347,198 A | 8/1982 | Ohkada et al. | 264/2.3 |
| 4,444,711 A | 4/1984 | Schad | 264/243 |
| 4,460,534 A | 7/1984 | Boehm et al. | 264/246 |
| 4,625,007 A | 11/1986 | Ellis et al. | 526/279 |
| 4,713,244 A | 12/1987 | Bawa | |
| 4,744,980 A | 5/1988 | Holly | 424/78 |
| 4,810,764 A | 3/1989 | Friends et al. | 526/245 |
| 4,883,658 A | 11/1989 | Holly | 424/80 |
| 4,910,277 A | 3/1990 | Bambury et al. | 526/260 |
| 5,177,165 A | 1/1993 | Valint, Jr. et al. | 526/245 |
| 5,266,563 A * | 11/1993 | Balazs et al. | 514/42 |
| 5,357,013 A | 10/1994 | Bambury et al. | 526/260 |
| 5,451,617 A | 9/1995 | Lai et al. | 523/107 |
| 5,508,317 A | 4/1996 | Muller | 522/85 |
| 5,534,605 A | 7/1996 | Bambury et al. | 526/260 |
| 5,573,934 A * | 11/1996 | Hubbell et al. | 435/177 |
| 5,583,163 A | 12/1996 | Mueller | 522/152 |
| 5,583,463 A | 12/1996 | Merritt | 327/526 |
| 5,665,840 A | 9/1997 | Pohlmann et al. | 526/264 |
| 5,712,356 A * | 1/1998 | Bothe et al. | 526/264 |
| 5,782,460 A | 7/1998 | Kretzschmar | |
| 5,789,464 A | 8/1998 | Muller | 523/108 |
| 5,843,346 A | 12/1998 | Morrill | 264/2.5 |
| 5,849,810 A | 12/1998 | Muller | 522/85 |
| 5,849,841 A | 12/1998 | Muhlebach et al. | 525/59 |
| 5,894,002 A | 4/1999 | Boneberger et al. | 264/1.36 |
| 5,932,674 A | 8/1999 | Müller | |
| 5,936,052 A | 8/1999 | Bothe et al. | 526/264 |
| 6,011,077 A | 1/2000 | Müller | |
| 6,039,913 A | 3/2000 | Hirt et al. | 264/331.11 |
| 6,107,365 A | 8/2000 | Bertozzi et al. | 523/106 |
| 6,165,408 A | 12/2000 | Steinmann | 264/496 |
| 6,221,303 B1 | 4/2001 | Steinmann | 264/496 |
| 6,303,687 B1 | 10/2001 | Muller | 525/61 |
| 6,367,929 B1 | 4/2002 | Maiden et al. | 351/160 H |
| 6,407,145 B1 | 6/2002 | Müller | |
| 6,440,366 B1 | 8/2002 | Salpekar et al. | 422/40 |
| 6,472,489 B1 | 10/2002 | Stockinger | 526/312 |
| 6,479,587 B1 | 11/2002 | Stockinger et al. | 525/131 |
| 6,492,478 B1 | 12/2002 | Steinmann | 526/258 |
| 6,552,103 B1 | 4/2003 | Bertozzi et al. | 523/106 |
| 6,627,124 B1 | 9/2003 | Herbrechtsmeier et al. | 264/1.36 |
| 6,713,717 B2 | 3/2004 | Takeda | 219/121.69 |
| 6,800,225 B1 | 10/2004 | Hagmann et al. | 264/1.36 |
| 6,822,016 B2 | 11/2004 | McCabe et al. | 523/107 |
| 6,940,580 B2 * | 9/2005 | Winterton et al. | 351/160 H |
| 6,943,203 B2 | 9/2005 | Vanderlaan et al. | 523/107 |
| 6,995,192 B2 | 2/2006 | Phelan et al. | 522/90 |
| 7,052,131 B2 | 5/2006 | McCabe et al. | 351/160 H |
| 7,091,283 B2 | 8/2006 | Muller et al. | 525/292 |
| 7,249,848 B2 | 7/2007 | Laredo et al. | 351/160 H |
| 2002/0182316 A1 | 12/2002 | Gilliard et al. | 427/162 |
| 2004/0116564 A1 | 6/2004 | Devlin | 524/241 |
| 2004/0140578 A1 | 7/2004 | Kelly et al. | 264/1.32 |
| 2004/0178541 A1 | 9/2004 | Kelly et al. | 264/496 |
| 2004/0214914 A1 | 10/2004 | Marmo | 523/106 |

(Continued)

FOREIGN PATENT DOCUMENTS

| | | |
|---|---|---|
| WO | WO 94/05257 | 3/1994 |
| WO | WO 96/24075 | 8/1996 |
| WO | 03022322 A2 | 3/2003 |

(Continued)

OTHER PUBLICATIONS

Breakspear S, Effect of the covalently linked faty acid 18-MEA on the nanotribology of hair's outermost surface, Journal of Structural Biology, 149, 2005, 235-242.*
International Search Report.
European Standard Search Report.

(Continued)

*Primary Examiner* — Celeste A Roney
(74) *Attorney, Agent, or Firm* — Sheng-Hsin Hu; Jian Zhou

(57) ABSTRACT

The invention relates to an ophthalmic product which has a capability of delivering a guest material (e.g., a lubricant or a drug) in a time-controlled-releasing manner. The invention also provides a process for making an ophthalmic product of the invention. In addition, the invention provides a method for time-controlled delivery of a drug or a lubricant.

9 Claims, 3 Drawing Sheets

(56) References Cited

U.S. PATENT DOCUMENTS

2004/0222539 A1 11/2004 Hagmann
2005/0113549 A1 5/2005 Devlin et al. .................. 528/44

FOREIGN PATENT DOCUMENTS

| WO | WO 2004/055148 | 7/2004 |
| WO | WO 2004/058489 | 7/2004 |
| WO | 2005092987 A1 | 10/2005 |

OTHER PUBLICATIONS

English Translation of Japan Office Action Notification of Reasons for Rejection, Dispatch No. 145901, Dispatch Date: Mar. 6, 2012, Japanese Patent Application No. 2008-509385.

* cited by examiner

OPHTHALMIC DEVICES FOR SUSTAINED DELIVERY OF ACTIVE COMPOUNDS

This application claims the benefits under 35 USC 119(e) of the U.S. Provisional Patent Application Nos. 60/677,964 filed May 5, 2005 and 60/719,878 filed Sep. 23, 2005, herein incorporated by reference in their entireties.

The present invention relates to ophthalmic devices, in particular contact lenses, which are capable of gradually releasing one or more guest materials during wear over at least about 6 hours after storing in a packaging solution for at least about one months. The present invention also provides methods for making ophthalmic devices of the invention and for time-controlled release of one or more guest materials for treating eye problems.

BACKGROUND OF THE INVENTION

Timed or controlled (or rather sustained) drug-delivery systems are well known in the pharmaceutical industry. However, this type of technology is not well known in the contact lens industry. This is partially due to the fact that most contact lenses are made from monomers polymerization (curing). Typically, polymerization of monomers is not very efficient; so that there remains a significant fraction of monomers after the "cure" is complete. Most of the time, these monomers could represent a serious health issue, so unpolymerized monomers are required to be extracted (i.e., removed) in an appropriate solvent extraction process using the formed contact lenses.

One problem associated with extraction is that this process is non-selective in its nature. Anything that is soluble in the employed solvent and is capable of leaching out of a formed contact lens; can (and usually will) be extracted. If there is a desired active compound or ingredient (e.g., a lubricant, a drug, etc.), all or most of the active compound or ingredient will also be removed in this extraction process, leaving a contact lens that is unable or inefficient in delivering the desired active compound or ingredient. In addition, in the extraction process, the lens is swollen so that any unbound moieties can be easily removed.

Industries have tried to overcome this problem by "loading" the polymerized article after-the-fact. This is accomplished by swelling the article in an appropriate solvent (much like in an extraction step) and then solubilizing the active compound/ingredient into that same solvent. After equilibrium, the loaded-product is removed from the solvent, allowed to dry to remove the solvent, or solvent exchanged to a solvent that does not solvate the loaded-active nor does it swell the polymer matrix; resulting in a dry-loaded article that is capable of releasing the desired compound or ingredient. However, there are several disadvantages associated with this "loading" process. First, it requires many additional steps, which can increase production costs. Second, its efficiency largely depends on the solubilization parameter of the compound or ingredient. Third, the article must be dried or solvent exchanged. In contrast, hydrogel contact lenses are stored in a packaging solution, in a hydrated state. Fourth, once the article is hydrated, the release mechanism is activated. Since hydrogel contact lenses are stored in a packaging solution, all or most (much) of the active compound or ingredient is already released in the packaging solution.

Therefore, there exist a need for methods for making hydrogel soft contact lenses capable of delivering an active compound in a sustainable manner over an extended period of time. There is also need for an ophthalmic device capable of delivering an active compound in a sustainable manner over an extended period of time.

SUMMARY OF THE INVENTION

The present invention, in one aspect, provides an ophthalmic product comprising a sealed package which include a packaging solution and a soft hydrogel contact lens, wherein the hydrogel contact lens comprises a polymer matrix and a guest material which is not covalently linked to the polymer matrix but distributed therein, wherein the hydrogel contact lens has a capability of gradually releasing the guest material during wear over at least about 6 hours after storing in the packaging solution for at least about one month, wherein the hydrogel contact lens is produced by cast-molding in a mold of a fluid prepolymer composition without being subjected to any extraction processes, wherein the prepolymer composition comprises the guest material and an actinically-crosslinkable prepolymer from which the polymer matrix is formed by polymerization, wherein the guest material is free of any groups capable of being thermally or actinically crosslinked with the actinically-crosslinkable prepolymer and present in an amount sufficient to be released from the contact lens over at least about 6 hours of wearing time.

The present invention, in another aspect, provides a process for making a soft contact lens capable of gradually delivering a guest material over an extended period of wearing time. The method of the invention comprises the steps of: a) obtaining a fluid prepolymer composition comprising an actinically-crosslinkable prepolymer and a guest material, wherein the actinically-crosslinkable prepolymer comprises ethylenically unsaturated groups and can be polymerized thermally or actinically to form the polymer matrix of the soft contact lens, wherein the guest material is free of any groups capable of being thermally or actinically crosslinked with the actinically-crosslinkable prepolymer, wherein the guest material is present in an amount sufficient to provide a desired functionality to the soft contact lens; b) introducing an amount of the fluid prepolymer composition in a mold for making a contact lens; c) polymerizing the actinically-crosslinkable prepolymer in the mold to form the soft contact lens with the guest material being not covalently linked to the polymer matrix but being distributed therein in a substantially uniform manner; d) packaging the resultant soft contact lens in a container containing a packaging solution; and e) sterilizing the soft contact lens in the package, wherein the sterilized soft contact lens is capable of gradually releasing the guest material during wear over at least about 6 hours, provided that the method is free of any extraction step.

The present invention, in a further aspect, provides a method for time-controlled delivery of a drug or a lubricant. The method of the invention comprises the steps of: a) obtaining a sealed package which include a packaging solution and a soft hydrogel contact lens which is obtained by cast-molding of a polymerizable composition in a mold, wherein the fluid polymerizable composition comprises a drug or lubricant without ethylenically unsaturated groups and at least one polymerizable component from the group consisting of a vinylic monomer, a macromer with one or more ethylenically unsaturated groups, an actinically-crosslinkable prepolymer with ethylenically unsaturated groups, and combinations thereof, wherein the polymer matrix of the contact lens is formed from thermal or actinic polymerization of ethylenically unsaturated groups in the polymerizable component, wherein the drug or lubricant is not covalently linked to the polymer matrix but being distributed therein, wherein the drug or lubricant is present in an amount sufficient to provide a desired functionality to the contact lens; b) wearing the soft hydrogel contact lens in an eye; and c) gradually delivering, under eye blinks, the drug or lubricant during wear over at least about 6 hours.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF THE INVENTION

Figure 1:
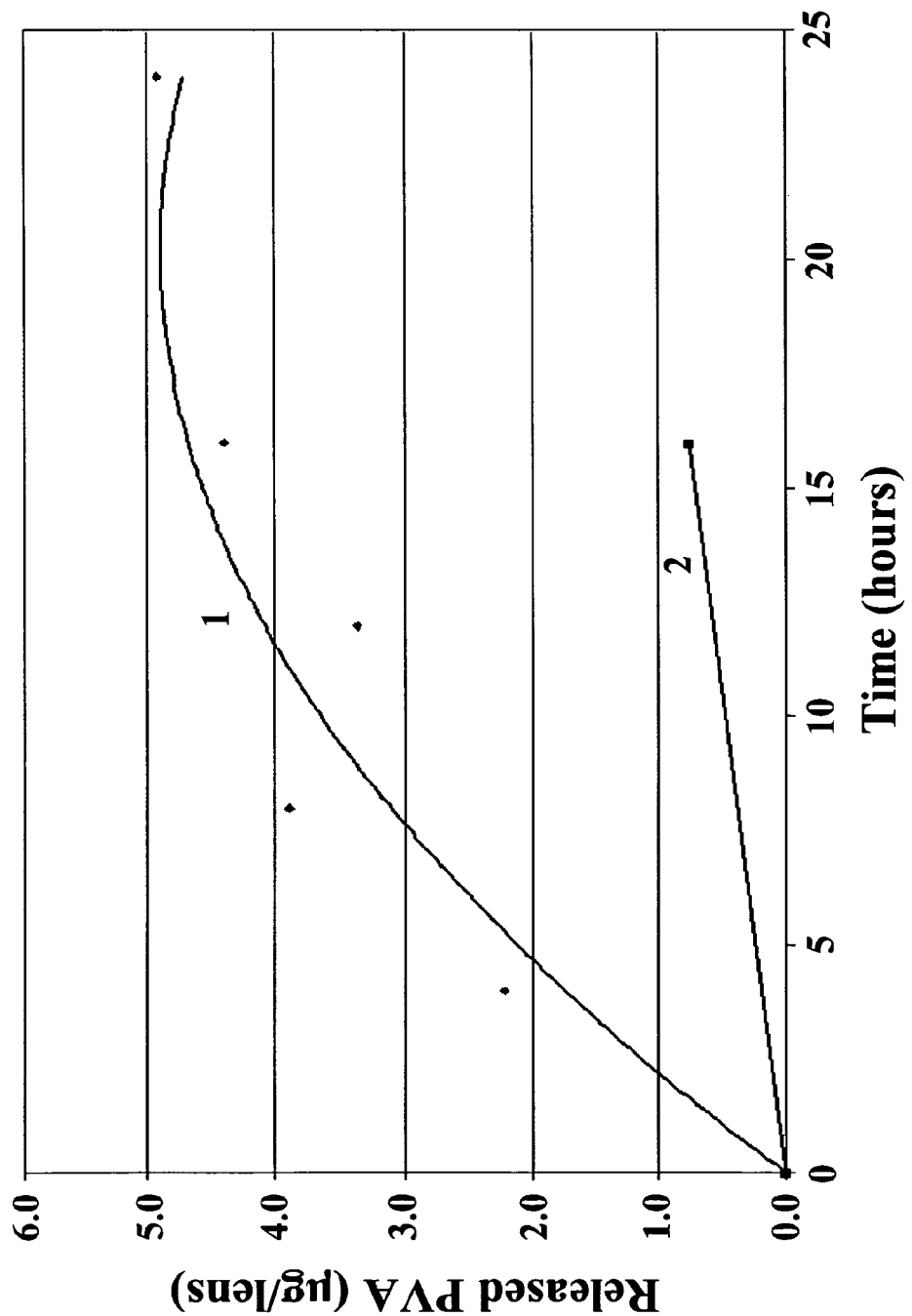
FIG. 1 shows extraction of non-crosslinkable PVAs from nelfilcon A contact lenses containing 1% (wt/v) of Mowiol 6-98 and Mowiol 10-98 PVAs (curve 1) and from control nelfilcon A contact lenses (curve 2).

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings.

A "hydrogel" refers to a polymeric material which can absorb at least 10 percent by weight of water when it is fully hydrated. A hydrogel material can be obtained by polymerization or copolymerization of at least one hydrophilic monomer in the presence of or in the absence of additional monomers and/or macromers or by crosslinking of a prepolymer.

A "silicone hydrogel" refers to a hydrogel obtained by copolymerization of a polymerizable composition comprising at least one silicone-containing vinylic monomer or at least one silicone-containing macromer or a silicone-containing prepolymer.

"Hydrophilic," as used herein, describes a material or portion thereof that will more readily associate with water than with lipids.

The term "fluid" as used herein indicates that a material is capable of flowing like a liquid.

A "monomer" means a low molecular weight compound that can be polymerized actinically or thermally or chemically. Low molecular weight typically means average molecular weights less than 700 Daltons.

As used herein, "actinically" in reference to curing or polymerizing of a polymerizable composition or material or a lens-forming material means that the curing (e.g., crosslinked and/or polymerized) is performed by actinic irradiation, such as, for example, UV irradiation, ionized radiation (e.g. gamma ray or X-ray irradiation), microwave irradiation, and the like. Thermal curing or actinic curing methods are well-known to a person skilled in the art. Lens-forming materials are well known to a person skilled in the art.

A "vinylic monomer", as used herein, refers to a low molecular weight compound that has an ethylenically unsaturated group and can be polymerized actinically or thermally. Low molecular weight typically means average molecular weights less than 700 Daltons.

The term "ethylenically unsaturated group" or "olefinically unsaturated group" is employed herein in a broad sense and is intended to encompass any groups containing at least one $>C=C<$ group. Exemplary ethylenically unsaturated groups include without limitation acryloyl, methacryloyl, allyl, vinyl, styrenyl, or other $C=C$ containing groups.

A "hydrophilic vinylic monomer", as used herein, refers to a vinylic monomer which is capable of forming a homopolymer that can absorb at least 10 percent by weight water when fully hydrated. Suitable hydrophilic monomers are, without this being an exhaustive list, hydroxyl-substituted lower alkyl ($C_1$ to $C_8$) acrylates and methacrylates, acrylamide, methacrylamide, (lower allyl)acrylamides and -methacrylamides, ethoxylated acrylates and methacrylates, hydroxyl-substituted (lower alkyl)acrylamides and -methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino(lower alkyl)-(where the term "amino" also includes quaternary ammonium), mono(lower alkylamino) (lower alkyl) and di(lower alkylamino)(lower alkyl)acrylates and methacrylates, allyl alcohol and the like.

A "hydrophobic vinylic monomer", as used herein, refers to a vinylic monomer which is capable of forming a homopolymer that can absorb less than 10 percent by weight water.

A "macromer" refers to a medium to high molecular weight compound or polymer that contains functional groups capable of undergoing further polymerizing/cross-linking reactions. Medium and high molecular weight typically means average molecular weights greater than 700 Daltons. Preferably, a macromer contains ethylenically unsaturated groups and can be polymerized actinically or thermally.

A "prepolymer" refers to a starting polymer which can be cured (e.g., crosslinked and/or polymerized) actinically or thermally or chemically to obtain a crosslinked and/or polymerized polymer having a molecular weight much higher than the starting polymer. A "actinically-crosslinkable prepolymer" refers to a starting polymer which can be crosslinked upon actinic radiation or heating to obtain a crosslinked polymer having a molecular weight much higher than the starting polymer. In accordance with the invention, an actinically-crosslinkable prepolymer should be soluble in a solvent and can be used in producing a finished lens of optical quality by cast-molding in a mold without the necessity for subsequent extraction.

"Visibility tinting" in reference to a lens means dying (or coloring) of a lens to enable the user to easily locate a lens in a clear solution within a lens storage, disinfecting or cleaning container. It is well known in the art that a dye and/or a pigment can be used in visibility tinting a lens.

"Dye" means a substance that is soluble in a solvent and that is used to impart color. Dyes are typically translucent and absorb but do not scatter light. Any suitable biocompatible dye can be used in the present invention.

A "Pigment" means a powdered substance that is suspended in a liquid in which it is insoluble. A pigment can be a fluorescent pigment, phosphorescent pigment, pearlescent pigment, or conventional pigment. While any suitable pigment may be employed, it is presently preferred that the pigment be heat resistant, non-toxic and insoluble in aqueous solutions.

"Guest materials" as used herein refer to any materials which are associated with or entrapped in or non-covalently bound to the polymer matrix of a contact lens. Exemplary guest materials include, without limitation, materials that impart desired functionalities to an ophthalmic device, for example, lubricants, drugs, proteins (such as enzymes or hormones or the likes), amino acids, nucleic acids, polypeptides, and the like.

As used herein the term "drugs" includes medicaments, therapeutics, vitamins, nutritional supplements, and the like. If the guest material is a drug, it is present in therapeutically effective amounts relative to its function. Any pharmaceutical drug can be utilized such as, for example, anti-cancer drugs, drug for central nerves, drugs for peripheral nerves, drugs for allergy, drugs for circulatory organs, drugs for respiratory organs, drugs for digestive organs, hormones, antibiotics, drugs for chemotherapy, natural moisturizing factors (NMFs), cutaneous lipids, vitamins, food supplements and the like.

It is known that natural moisturizing factors, cutaneous lipids and some other materials play some critical roles in maintaining the level of hydration necessary for the healthy functional of the skin. Such materials can also be used to increase hydration level in the eye. Examples of ophthalmically beneficial materials useful for maintaining hydration level in the eye include without limitation 2-pyrrolidone-5-carboxylic acid (PCA), amino acids (e.g., taurine, glycine, etc.), alpha hydroxyl acids (e.g., glycolic, lactic, malic, tartaric, mandelic and citric acids and salts thereof, etc.), linoleic and gamma linoleic acids, and vitamins (e.g., B5, A, B6, etc.).

"Lubricants" as used herein refer to any compounds or materials which can enhance surface wettability of a contact lens and/or the eye or reduce the frictional character of the contact lens surface.

The term "time-controlled-release" or "time-controlled-releasing manner" in reference to a guest material being released from an ophthalmic device (e.g., a contact lens) is intended to describe an eye-blink-activated leaching process in which the guest material is gradually released under actions of eye-blinking. In accordance with the invention, eye-blink-activated gradual release of a guest material from a contact lens is characterized based on an in vitro release model (in vitro eye-blink-activated release simulating experiment) described in Example 1.

The present invention is generally directed to an ophthalmic product which has a capability of delivering a guest material (e.g., a lubricant or a drug) in a time-controlled-releasing manner. The present invention is partly based on the discovery that a leachable guest material, e.g., leachable high molecular weight PVAs can be easily incorporated into a hydrogel contact lens made a solution of a prepolymer (e.g., actinically-crosslinkable PVAs) in a cast-molding process without any extraction process. Without extraction, there is no need to "load" the resultant hydrogel contact lens with the guest material after-the-fact. The present invention is also partly based on the discovery that under the laboratory conditions and without agitation, it is extremely difficult to completely extract out of all of the leachable PVAs incorporated in a hydrogel lens with a packaging solution (e.g., a buffered saline) and that a hydrogel lens of the invention, which has leachable high molecular weight PVAs incorporated and distributed in the polymer matrix of the lens, can still impart wearer comfort over a prolonged period of time even after extraction with saline or storing in a packaging solution (buffered saline) for a long time (e.g., up to about 5 years). It is believed that polymer chains of leachable PVAs entangle with the polymer matrix of a soft hydrogel lens and there may have interactions, such as, e.g., hydrophobic/hydrophobic interactions, ionic interactions, hydrogen bonding between leachable PVAs and the polymer matrix of the lens. With such interactions and polymer chain entanglement, passive diffusion of leachable PVAs out of a hydrogel lens is kinetically unfavorable and extremely slow. However, eye-blinking may provide enough energy needed for some PVA molecule to diffuse out of a hydrogel lens. It is understood that when a hydrogel lens is worn by a patient, the ocular environment may also provide some thermal energy which can also facilitate leaching of leachable PVAs out of the lens. With such eye-blink-activated release mechanism, a hydrogel contact lens with leachable PVAs incorporated therein can provide prolonged wearer comfort and in particular end-of-day comfort even after stored in a packaging solution for an extended period of time, e.g., up to about 5 years.

In one aspect, the invention provides an ophthalmic product comprising a sealed package which include a packaging solution and a soft hydrogel contact lens, wherein the hydrogel contact lens comprises a polymer matrix and a guest material which is not covalently linked to the polymer matrix but distributed therein, wherein the hydrogel contact lens has a capability of gradually releasing the guest material during wear over at least about 6 hours after storing in the packaging solution for at least about one month, wherein the hydrogel contact lens is produced by cast-molding in a mold of a fluid prepolymer composition without being subjected to any extraction processes, wherein the prepolymer composition comprises the guest material and an actinically-crosslinkable prepolymer from which the polymer matrix is formed by polymerization, wherein the guest material is free of any groups capable of being thermally or actinically crosslinked with the actinically-crosslinkable prepolymer and present in an amount sufficient to be released from the contact lens over at least about 6 hours of wearing time.

In accordance with the present invention, a fluid prepolymer composition comprises at least one guest material and at least one actinically-crosslinkable prepolymer. It can be a solution, a solvent-free liquid, or a melt and comprises an actinically-crosslinkable. Preferably, a fluid prepolymer composition is a solution of at least one actinically prepolymer. More preferably, a fluid prepolymer composition is an aqueous solution of at least one actinically-crosslinkable prepolymer. It is understood that a fluid prepolymer composition can also comprise one or more vinylic monomers, one or more vinylic macromers, and/or one or more cross-linking agents. However, the amount of those components should be so small that a hydrogel lens made from the fluid prepolymer composition does not contain unacceptable levels of unpolymerized monomers, macromers and/or crosslinking agents. The presence of unacceptable levels of unpolymerized monomers, macromers and/or crosslinking agents will require extraction to remove them. Similarly, a fluid prepolymer composition can further comprise various components, such as polymerization initiators (e.g., photoinitiator or thermal initiator), photosensitizers, inhibitors, fillers, and the like, so long their presence in a lens does not require the lens to be subjected any extraction treatment.

Examples of suitable photoinitiators are benzoin methyl ether, 1-hydroxycyclohexyl-phenyl ketone, or Darocure® or Irgacure® types, for example Darocure® 1173 or Irgacure® 2959. The amount of photoinitiator may be selected within wide limits, an amount of up to 0.05 g/g of prepolymer and especially of up to 0.003 g/g of prepolymer having proved beneficial. A person skilled in the art will know well how to select a photoinitiator.

The solution of the prepolymer and the guest material defined hereinbefore is preferably a pure solution which means a solution which is free or essentially free from undesired constituents, for example, free from monomeric, oligomeric or polymeric starting compounds used for the preparation of the prepolymer, and/or free from secondary products formed during the preparation of the prepolymer.

A further solvent of the aqueous prepolymer solution may be, for example an alcohol, such as methanol, ethanol or n- or iso-propanol, or a carboxylic acid amide, such as N,N-dimethylformamide, or dimethyl sulfoxide. The aqueous solution preferably contains no further solvent.

The aqueous solution of the prepolymer preferably does not contain a comonomer that needs to be removed after the article is formed.

A solution of at least one actinically-crosslinkable prepolymer can be prepared by dissolving the actinically-crosslinkable prepolymer and other components in any suitable solvent known to a person skilled in the art. Examples of suitable solvents are water, alcohols, such as lower alkanols, for example ethanol or methanol, and furthermore carboxylic acid amides, such as dimethylformamide, dipolar aprotic solvents, such as dimethyl sulfoxide or methyl ethyl ketone, ketones, for example acetone or cyclohexanone, hydrocarbons, for example toluene, ethers, for example THF, dimethoxyethane or dioxane, and halogenated hydrocarbons, for example trichloroethane, and also mixtures of suitable solvents, for example mixtures of water with an alcohol, for example a water/ethanol or a water/methanol mixture.

A preferred group of prepolymers are those which are soluble in water, a water-organic solvent mixture and an organic solvent, meltable at a temperature below about 85° C., and are ophthalmically compatible. It would be advantageous that an actinically-crosslinkable prepolymer are in a substantially pure form (e.g., purified by ultrafiltration to remove most reactants for forming the prepolymer). Therefore, after crosslinking by actinic radiation, a medical device, preferably an ophthalmic device may require practically no more subsequent purification, such as in particular complicated extraction of unpolymerized constituents. Furthermore, crosslinking may take place solvent-free or in aqueous solution, so that a subsequent solvent exchange or the hydration step is not necessary.

Examples of preferred actinically crosslinkable prepolymers include, but are not limited to, a water-soluble crosslinkable poly(vinyl alcohol) prepolymer described in U.S. Pat. Nos. 5,583,163 and 6,303,687 (incorporated by reference in their entireties); a water-soluble vinyl group-terminated polyurethane prepolymer described in U.S. Patent Application Publication No. 2004/0082680 (herein incorporated by reference in its entirety); derivatives of a polyvinyl alcohol, polyethyleneimine or polyvinylamine, which are disclosed in U.S. Pat. No. 5,849,841 (incorporated by reference in its entirety); a water-soluble crosslinkable polyurea prepolymer described in U.S. Pat. No. 6,479,587 and in commonly owned pending U.S. patent application Ser. No. 10/991,124 filed on Nov. 17, 2004 (herein incorporated by reference in their entireties); crosslinkable polyacrylamide; crosslinkable statistical copolymers of vinyl lactam, MMA and a comonomer, which are disclosed in EP 655,470 and U.S. Pat. No. 5,712,356; crosslinkable copolymers of vinyl lactam, vinyl acetate and vinyl alcohol, which are disclosed in EP 712,867 and U.S. Pat. No. 5,665,840; polyether-polyester copolymers with crosslinkable side chains which are disclosed in EP 932,635 and U.S. Pat. No. 6,492,478; branched polyalkylene glycol-urethane prepolymers disclosed in EP 958,315 and U.S. Pat. No. 6,165,408; polyalkylene glycol-tetra(meth)acrylate prepolymers disclosed in EP 961,941 and U.S. Pat. No. 6,221,303; and crosslinkable polyallylamine gluconolactone prepolymers disclosed in PCT patent application WO 2000/31150 and U.S. Pat. No. 6,472,489.

Examples of silicone-containing prepolymers are those described in commonly-owned US Published Patent Application No. US 2001-0037001 A1 and U.S. Pat. No. 6,039,913, which are incorporated herein by references in their entireties.

In a preferred embodiment, an actinically-crosslinkable prepolymer is a water-soluble crosslinkable poly(vinyl alcohol). More preferably, a water-soluble crosslinkable poly(vinyl alcohol) prepolymer is a polyhydroxyl compound which is described in U.S. Pat. Nos. 5,583,163 and 6,303,687 and has a molecular weight of at least about 2000 and which comprises from about 0.5 to about 80%, based on the number of hydroxyl groups in the poly(vinyl alcohol), of units of the formula I, I and II, I and III, or I and II and III

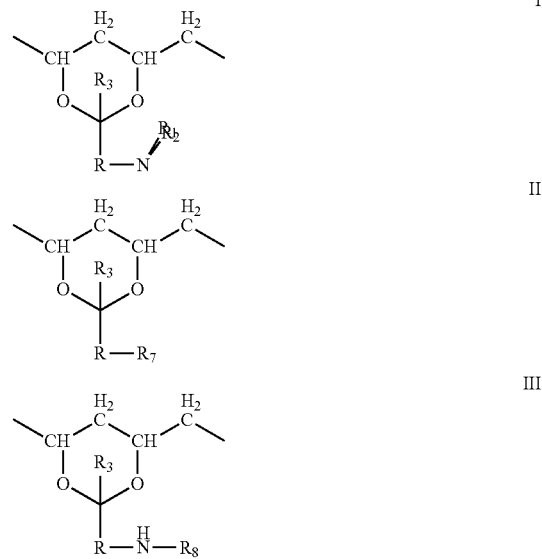

In formula I, II and III, the molecular weight refers to a weight average molecular weight, Mw, determined by gel permeation chromatography.

In formula I, II and III, $R_3$ is hydrogen, a $C_1$-$C_6$ alkyl group or a cycloalkyl group.

In formula I, II and II, R is alkylene having up to 12 carbon atoms, preferably up to 8 carbon atoms, and can be linear or branched. Suitable examples include octylene, hexylene, pentylene, butylene, propylene, ethylene, methylene, 2-propylene, 2-butylene and 3-pentylene. Lower alkylene R preferably has up to 6, particularly preferably up to 4 carbon atoms. Methylene and butylene are particularly preferred.

In the formula I, $R_1$ is hydrogen or lower alkyl having up to seven, in particular up to four, carbon atoms. Most preferably, $R_1$ is hydrogen.

In the formula I, $R_2$ is an olefinically unsaturated, electron-withdrawing, crosslinkable radical, preferably having up to 25 carbon atoms. In one embodiment, $R_2$ is an olefinically unsaturated acyl radical of the formula $R_4$—CO—, in which $R_4$ is an olefinically unsaturated, crosslinkable radical having 2 to 24 carbon atoms, preferably having 2 to 8 carbon atoms, particularly preferably having 2 to 4 carbon atoms.

The olefinically unsaturated, crosslinkable radical $R_4$ having 2 to 24 carbon atoms is preferably alkenyl having 2 to 24 carbon atoms, in particular alkenyl having 2 to 8 carbon atoms, particularly preferably alkenyl having 2 to 4 carbon atoms, for example ethenyl, 2-propenyl, 3-propenyl, 2-butenyl, hexenyl, octenyl or dodecenyl. Ethenyl and 2-propenyl are preferred, so that the —CO—$R_4$ group is the acyl radical of acrylic acid or methacrylic acid.

In the formula II, $R_7$ is a primary, secondary or tertiary amino group or a quaternary amino group of the formula $N^+(R')_3X^-$, in which each R', independently of the others, is hydrogen or a $C_1$-$C_4$ alkyl radical and X is a counterion, for example $HSO_4^-$, $F^-$, $Cl^-$, $Br^-$, $I^-$, $CH_3COO^-$, $OH^-$, $BF^-$, or $H_2PO_4^-$. The radicals $R_7$ are, in particular, amino, mono- or di(lower alkyl)amino, mono- or diphenylamino, (lower alkyl)phenylamino or tertiary amino incorporated into a heterocyclic ring, for example —$NH_2$, —NH—$CH_3$, —$N(CH_3)_2$, —$NH(C_2H_5)$, —$N(C_2H_5)_2$, —NH(phenyl), —$N(C_2H_5)$phenyl or

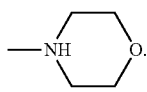

In the formula III, $R_8$ is the radical of a monobasic, dibasic or tribasic, saturated or unsaturated, aliphatic or aromatic organic acid or sulfonic acid. Preferred radicals $R_8$ are derived, for example, from chloroacetic acid, succinic acid, glutaric acid, adipic acid, pimelic acid, maleic acid, fumaric acid, itaconic acid, citraconic acid, acrylic acid, methacrylic acid, phthalic acid and trimellitic acid.

For the purposes of this invention, the term "lower" in connection with radicals and compounds denotes, unless defined otherwise, radicals or compounds having up to 7 carbon atoms, preferably having up to 4 carbon atoms.

Lower alkyl has, in particular, up to 7 carbon atoms, preferably up to 4 carbon atoms, and is, for example, methyl, ethyl, propyl, butyl or tert-butyl.

Lower alkoxy has, in particular, up to 7 carbon atoms, preferably up to 4 carbon atoms, and is, for example, methoxy, ethoxy, propoxy, butoxy or tert-butoxy.

In the formula $N^+(R')_3X^-$, R' is preferably hydrogen or $C_1$-$C_3$ alkyl, and X is halide, acetate or phosphite, for example —$N^+(C_2H_5)_3CH_3COO^-$, —$N^+(C_2H_5)_3Cl^-$, and —$N^+(C_2H_5)_3H_2PO_4^-$.

A water-soluble crosslinkable poly(vinyl alcohol) according to the invention is more preferably a polyhydroxyl compound which has a molecular weight of at least about 2000 and which comprises from about 0.5 to about 80%, preferably from 1 to 50%, more preferably from 1 to 25%, even more preferably from 2 to 15%, based on the number of hydroxyl groups in the poly(vinyl alcohol), of units of the formula I, wherein R is lower alkylene having up to 6 carbon atoms, $R_1$ is hydrogen or lower alkyl, $R_3$ is hydrogen, and $R_2$ is a radical of formula (V). Where p is zero, $R_4$ is preferably $C_2$-$C_8$ alkenyl. Where p is one and q is zero, $R_6$ is preferably $C_2$-$C_6$ alkylene and $R_4$ is preferably $C_2$-$C_8$ alkenyl. Where both p and q are one, $R_5$ is preferably $C_2$-$C_6$ alkylene, phenylene, unsubstituted or lower alkyl-substituted cyclohexylene or cyclo hexylene-lower alkylene, unsubstituted or lower alkyl-substituted phenylene-lower alkylene, lower alkylene-phenylene, or phenylene-lower alkylene-phenylene, $R_6$ is preferably $C_2$-$C_6$ alkylene, and $R_4$ is preferably $C_2$-$C_8$ alkenyl.

Crosslinkable poly(vinyl alcohol)s comprising units of the formula I, I and II, I and III, or I and II and III can be prepared in a manner known per se. For example, U.S. Pat. Nos. 5,583,163 and 6,303,687 disclose and teach how to prepare crosslinkable polymers comprising units of the formula I, I and II, I and III, or I and II and III.

In another preferred embodiment, an actinically-crosslinkable prepolymer is a crosslinkable polyurea as described in U.S. Pat. No. 6,479,587 or in a commonly assigned copending U.S. patent application Ser. No. 10/991,124 filed on Nov. 17, 2004 (herein incorporated by reference in their entireties).

A preferred crosslinkable polyurea prepolymer has formula (1)

$$CP—(Q)_q \tag{1}$$

wherein q is an integer of ≥3, Q is an organic radical that comprises at least one crosslinkable group, CP is a multivalent branched copolymer fragment comprising segments A and U and optionally segments B and T, wherein: A is a bivalent radical of formula $$—NR_A\text{-}A_1\text{-}NR_A'— \tag{2}$$

wherein $A_1$ is the bivalent radical of —$(R_{11}—O)_n$—$(R_{12}—O)_m$—$(R_{13}—O)_p$—, a linear or branched $C_2$-$C_{24}$ aliphatic bivalent radical, a $C_5$-$C_{24}$ cycloaliphatic or aliphatic-cycloaliphatic bivalent radical, or a $C_6$-$C_{24}$ aromatic or araliphatic bivalent radical, $R_{11}$, $R_{12}$, $R_{13}$, independently of one other, are each linear or branched $C_2$-$C_4$-alkylene or hydroxy-substituted $C_2$-$C_8$ alkylene radical, n, m and p, independently of one another, are each a number from 0 to 100, provided that the sum of (n+m+p) is 5 to 1000, and $R_A$ and $R_A'$ independently of each other is hydrogen, an unsubstituted $C_1$-$C_6$alkyl, a substituted $C_1$-$C_6$alkyl, or a direct, ring-forming bond;

T is a bivalent radical of formula

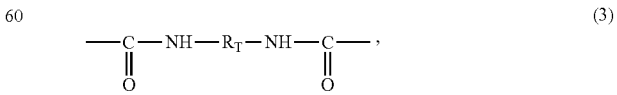

wherein $R_T$ is a bivalent aliphatic, cycloaliphatic, aliphatic-cycloaliphatic, aromatic, araliphatic or aliphatic-heterocyclic radical;

U is a trivalent radical of formula

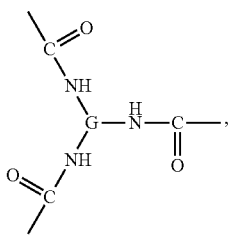

(4)

wherein G is a linear or branched $C_3$-$C_{24}$ aliphatic trivalent radical, a $C_5$-$C_{45}$ cycloaliphatic or aliphatic-cycloaliphatic trivalent radical, or a $C_3$-$C_{24}$ aromatic or araliphatic trivalent radical;

B is a radical of formula $$-NR_B-B1-NR_B'- \quad (5)$$

wherein $R_B$ and $R_B'$ independently of each other is hydrogen, an unsubstituted $C_1$-$C_6$alkyl, a substituted $C_1$-$C_6$alkyl, or a direct, ring-forming bond, $B_1$ is a bivalent aliphatic, cycloaliphatic, aliphatic-cycloaliphatic, aromatic or araliphatic hydrocarbon radical that is interrupted by at least one amine group —$NR_m$— in which $R_m$ is hydrogen, a radical Q mentioned above or a radical of formula $$Q\text{-}CP'- \quad (6),$$

wherein Q is as defined above, and CP' is a bivalent copolymer fragment comprising at least two of the above-mentioned segments A, B, T and U; provided that in the copolymer fragments CP and CP' a segment A or B is followed by a segment T or U in each case; provided that in the copolymer fragments CP and CP' a segment T or U is followed by a segment A or B in each case; provided that the radical Q in formulae (1) and (6) is bonded to a segment A or B in each case; and provided that the N atom of —$NR_m$— is bonded to a segment T or U when $R_m$ is a radical of formula (6).

A crosslinkable prepolymer of formula (1) is obtained by introducing ethylenically unsaturated groups into an amine- or isocyanate-capped polyurea, which preferably is a copolymerization product of a mixture comprising (a) at least one poly(oxyalkylene)diamine, (b) at least one organic polyamine, (c) optionally at least one diisocyanate, and (d) at least one polyisocyanate. More preferably, the amine- or isocyanate-capped polyurea is a copolymerization product of a mixture comprising (a) at least one poly(oxyalkylene) diamine, (b) at least one organic di- or poly-amine (preferably triamine), (c) at least one diisocyanate, and (d) at least one polyisocyanate (preferably triisocyanate).

Examples of preferred poly(oxyalkylene)diamine include so-called Jeffamines® having an average molecular weight of, for example, approximately from 200 to 5000.

Diisocyanate can be a linear or branched $C_3$-$C_{24}$ aliphatic diisocyanate, a $C_5$-$C_{24}$ cycloaliphatic or aliphatic-cycloaliphatic diisocyanate, or a $C_6$-$C_{24}$ aromatic or araliphatic diisocyanate. Examples of especially preferred diisocyanates are isophorone diisocyanate (IPDI), 4,4'-methylenebis (cyclohexyl isocyanate), toluylene-2,4-diisocyanate (TDI), 1,6-diisocyanato-2,2,4-trimethyl-n-hexane (TMDI), methylenebis(cyclohexyl-4-isocyanate), methylenebis(phenyl-isocyanate) or hexamethylene-diisocyanate (HMDI).

An organic diamine can be a linear or branched $C_2$-$C_{24}$ aliphatic diamine, a $C_5$-$C_{24}$ cycloaliphatic or aliphatic-cycloaliphatic diamine, or a $C_6$-$C_{24}$ aromatic or araliphatic diamine. A preferred organic diamine is bis(hydroxyethylene)ethylenediamine (BHEEDA).

Examples of preferred polyamines are symmetrical or asymmetrical dialkylenetriamines or trialkylenetetramines. Preferred polyamines include without limitation diethylenetriamine, N-2'-aminoethyl-1,3-propylenediamine, N,N-bis (3-aminopropyl)-amine, N,N-bis(6-aminohexyl)amine and triethylenetetramine.

A polyisocyanate can be a linear or branched $C_3$-$C_{24}$ aliphatic polyisocyanate, a $C_5$-$C_{45}$ cycloaliphatic or aliphatic-cycloaliphatic polyisocyanate, or a $C_6$-$C_{24}$ aromatic or araliphatic polyisocyanate. Preferably, a polyisocyanate is a $C_6$-$C_{45}$ cycloaliphatic or aliphatic-cycloaliphatic compound containing 3-6 isocyanate groups and at least one heteroatom selected from the group consisting of oxygen and nitrogen. More preferably, a polyisocyanate is a compound having a group of formula (7):

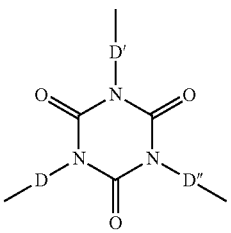

(7)

wherein D, D' and D" independent of one another are a linear or branched divalent $C_1$-$C_{12}$ alkyl radical, a divalent $C_5$-$C_{14}$ alkylcycloalkyl radical. Examples of preferred triisocyanates include without limitation the isocyanurate trimer of hexamethylene diisocyanate, 2,4,6-toluene triisocyanate, p, p', p"-triphenylmethane triisocyanate, and the trifunctional trimer (isocyanurate) of isophorone diisocyanate.

It is advantageous that the amine- or isocyanate-capped polyurea is an amine-capped polyurea which may allow the second step reaction to be carried out in an aqueous medium.

A crosslinkable polyurea prepolymer of the invention can be prepared in a manner known to persons skilled in the art, for example in a two-step process. In the first step, an amine- or isocyanate-capped polyurea of the invention is prepared by reacting together a mixture comprising (a) at least one poly(oxyalkylene)diamine, (b) at least one organic di- or poly-amine, (c) at least one diisocyanate, and (d) at least one polyisocyanate. In the second step, a multifunctional compound having at least one ethylenically unsaturated group and a function group co-reactive with the capping amine or isocyanate groups of the amine- or isocyanate-capped polyurea obtained in the first step.

The first step reaction is advantageously carried out in an aqueous or aqueous-organic medium or organic solvent (e.g. ethyllactate, THF, isopropanol, or the like). A suitable medium has been found to be especially a mixture of water and a readily water-soluble organic solvent, e.g. an alkanol, such as methanol, ethanol or isopropanol, a cyclic ether, such as tetrahydrofuran (THF), or a ketone, such as acetone. An especially suitable reaction medium is a mixture of water and a readily water-soluble solvent having a boiling point of from 50 to 85° C., preferably from 50 to 70° C., especially a water/tetrahydrofuran or a water/acetone mixture.

The reaction temperature in the first reaction step of the process is, for example, from −20 to 85° C., preferably from −10 to 50° C. and most preferably from −5 to 30° C.

The reaction times in the first reaction step of the process may vary within wide limits, a time of approximately from 1 to 10 hours, preferably from 2 to 8 hours and most preferably 2 to 3 hours having proved practicable.

In accordance with the invention, the criterion that the prepolymer is soluble in water denotes in particular that the prepolymer is soluble in a concentration of approximately from 3 to 90% by weight, preferably approximately from 5 to 60% by weight, especially approximately from 10 to 60% by weight, in a substantially aqueous solution. Insofar as it is possible in an individual case, prepolymer concentrations of more than 90% are also included in accordance with the invention. Especially preferred concentrations of the prepolymer in solution are from approximately 15 to approximately 50% by weight, especially from approximately 15 to approximately 40% by weight, for example from approximately 25% to approximately 40% by weight.

Preferably, the prepolymers used in the process according to the invention are previously purified in a manner known per se, for example by precipitation with organic solvents, such as acetone, filtration and washing, extraction in a suitable solvent, dialysis or ultrafiltration, ultrafiltration being especially preferred. By means of that purification process the prepolymers can be obtained in extremely pure form, for example in the form of concentrated aqueous solutions that are free, or at least substantially free, from reaction products, such as salts, and from starting materials, such as, for example, non-polymeric constituents.

The preferred purification process for the prepolymers used in the process according to the invention, ultrafiltration, can be carried out in a manner known per se. It is possible for the ultrafiltration to be carried out repeatedly, for example from two to ten times. Alternatively, the ultrafiltration can be carried out continuously until the selected degree of purity is attained. The selected degree of purity can in principle be as high as desired. A suitable measure for the degree of purity is, for example, the concentration of dissolved salts obtained as by-products, which can be determined simply in known manner.

In accordance with the invention, a guest material is a lubricant, ocular salve, thickening agent, a drug, ophthalmically beneficial materials, or mixtures thereof. Preferably, a guest material has a kinetically-unfavorable (passive) diffusion out of a lens of the invention, characterized by a ratio of eye blink-activated diffusion to passive diffusion being about 1.2 or greater, preferably about 1.6 or greater, more preferably about 2.0 or greater, even more preferably about 2.4 or greater, determined after a cumulative extraction period of at least about 3 hours, preferably at least about 4 hours.

The term "passive diffusion" is intended to describe a diffusion process in which no external energy (such as, for example, pressure, kinetic energy from agitation, or thermal energy in excess of normal room temperature of about 20-25° C.) is provided. Passive diffusion can be determined by determining the cumulative concentration of a guest material after a series of extractions from a hydrogel lens containing the guest material. Each extraction is carried out as follows. A contact lens is first blotted dry and immediately is carefully placed into 100 µl of an extraction medium (water or saline or buffered saline) in an tube (e.g., a centrifuge tube, a scintillation vial, or preferably an Eppendorf microtube). Each extraction lasts about one hour and maintained at room temperature (e.g., 25° C.) without agitation. The extraction medium is removed from the Eppendorf microtube and 100 µl of a fresh extraction medium is added. The value of extraction volume per hour (100 µl) is estimated based on tear flow rate of the eye (ca. 1-15 µl/min). Extraction medium should be a water-based liquid, i.e., water or an aqueous solution. A cumulative extraction period refers to a total time equal to (the number of consecutive extractions)–(the extraction period of each extraction). For example, a cumulative extraction period of three hours is the total time of three consecutive extractions.

The term "eye blink-activated diffusion" is intended to describe a diffusion process in which eye blinks provide energy to facilitate a guest material diffusion out of a polymer matrix. In accordance with the invention, eye blink-activated diffusion is determined by using an in vitro in-eye release model (in vitro eye blink-activated release simulating experiment). A contact lens is first blotted dry and immediately is carefully placed into 100 µl of an extraction medium in an tube (e.g., a centrifuge tube, a scintillation vial, or preferably an Eppendorf microtube) and the microtube is agitated for fifteen seconds using, e.g., a Vibrex vortex mixer. At the end of one hour period, the tube is again agitated using, e.g., a Vibrex vortex mixer, for a further fifteen seconds. The extraction medium is removed from the Eppendorf microtube and 100 µl of a fresh extraction medium is added. Extraction samples are stored at 25° C. between agitation procedures. The concentration of a guest material extracted out of a lens can be determined according to any methods known to a person skilled in the art.

In accordance with the invention, a ratio of eye blink-activated diffusion to passive diffusion is calculated based on the results of above-described passive and eye blink-activated diffusion experiments carried out under substantially identical temperature and cumulative extraction period. It is understood that passive diffusion and eye blink-activated diffusion each are obtained by averaging results of at least three parallel experiments each done with one lens.

Ratio of eye blink-activated diffusion to passive diffusion for a given guest material depends largely on the structure of the guest material. If a guest material has a long polymer chain or a highly branched polymer, passive diffusion for this guest material may be low and therefore ratio of eye blink-activated diffusion to passive diffusion for this guest material may be high. Similarly, if a guest material has strong interactions with the polymer matrix of a hydrogel lens, passive diffusion for this guest material may be low and subsequently ratio of eye blink-activated diffusion to passive diffusion for this guest material may be high. In addition, a guest material has a much higher solubility in the polymer matrix of a hydrogel lens than in an extraction medium.

Examples of lubricants include without limitation mucin-like materials and hydrophilic polymers.

Exemplary mucin-like materials include without limitation polyglycolic acid, polylactides, collagen, and gelatin. A mucin-like material can be used as guest materials which can be released continuously and slowly over extended period of time to the ocular surface of the eye for treating dry eye syndrome. The mucin-like material preferably is present in effective amounts.

Exemplary hydrophilic polymers include, but are not limited to, polyvinylalcohols (PVAs), polyamides, polyimides, polylactone, a homopolymer of a vinyl lactam, a copolymer of at least one vinyl lactam in the presence or in the absence of one or more hydrophilic vinylic comonomers, a homopolymer of acrylamide or methaacrylamide, a copolymer of acrylamide or methacrylamide with one or more hydrophilic vinylic monomers, mixtures thereof.

Exemplary ophthalmically beneficial materials include without limitation 2-pyrrolidone-5-carboxylic acid (PCA), amino acids (e.g., taurine, glycine, etc.), alpha hydroxyl acids (e.g., glycolic, lactic, malic, tartaric, mandelic and citric acids and salts thereof, etc.), linoleic and gamma linoleic acids, and vitamins (e.g., B5, A, B6, etc.).

A guest material is present in the fluid prepolymer composition in an amount of, for example, from 0.05 to 10% by weight, preferably from 0.1 to 5.0% by weight, more preferably from 0.25 to 3% by weight, and in particular from 0.4 to 1.2% by weight, each based on the entire weight of the composition.

The vinyl lactam has a structure of formula (I)

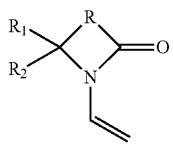

wherein
R is an alkylene di-radical having from 2 to 8 carbon atoms,
$R_1$ is hydrogen, alkyl, aryl, aralkyl or alkaryl, preferably hydrogen or lower alkyl having up to 7 and, more preferably, up to 4 carbon atoms, such as, for example, methyl, ethyl or propyl; aryl having up to 10 carbon atoms, and also aralkyl or alkaryl having up to 14 carbon atoms; and
$R_2$ is hydrogen or lower alkyl having up to 7 and, more preferably, up to 4 carbon atoms, such as, for example, methyl, ethyl or propyl.

Some N-vinyl lactams corresponding to the above structural formula (I) are N-vinyl-2-pyrrolidone, N-vinyl-2-piperidone, N-vinyl-2-caprolactam, N-vinyl-3-methyl-2-pyrrolidone, N-vinyl-3-methyl-2-piperidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5-methyl-2-piperidone, N-vinyl-5,5-dimethyl-2-pyrrolidone, N-vinyl-3,3,5-trimethyl-2-pyrrolidone, N-vinyl-5-methyl-5-ethyl-2-pyrrolidone, N-vinyl-3,4,5-trimethyl-3-ethyl-2-pyrrolidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam and N-vinyl-3,5,7-trimethyl-2-caprolactam.

The number-average molecular weight $M_n$ of a hydrophilic polymer is, for example, higher by at least 10000, preferably by at least 20000, than that of the actinically-crosslinkable prepolymer. For example, in the preferred case of a water-soluble prepolymer having an average molecular weight $M_n$ of from 12000 to 25000, the average molecular weight $M_n$ of the hydrophilic polymer is, for example, from 25000 to 100000, preferably from 30000 to 75000 and in particular from 35000 to 70000.

Examples of hydrophilic polymers include but are not limited to polyvinylalcohol (PVA), polyethylene oxide (i.e., polyethyleneglycol (PEG)), poly-N-vinyl pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, and poly-N-vinyl-4,5-dimethyl-2-pyrrolidone, polyvinylimidazole, poly-N—N-dimethylacrylamide, poly-acrylic acid, poly 2 ethyl oxazoline, heparin polysaccharides, polysaccharides, a polyoxyethylene derivative, mixtures thereof.

A suitable polyoxyethylene derivative is, for example, a n-alkylphenyl polyoxyethylene ether, n-alkyl polyoxy-ethylene ether (e.g., TRITON®), polyglycol ether surfactant (TERGITOL®), polyoxyethylenesorbitan (e.g., TWEEN®), polyoxyethylated glycol monoether (e.g., BRIJ®, polyoxylethylene 9 lauryl ether, polyoxylethylene 10 ether, polyoxylethylene 10 tridecyl ether), or a block copolymer of ethylene oxide and propylene oxide (e.g. poloxamers or poloxamines).

A class of preferred polyoxyethylene derivatives used in the present invention are polyethylene-polypropylene block copolymers, in particular poloxamers or poloxamines which are available, for example, under the tradename PLURONIC®, PLURONIC-R®, TETRONIC®, TETRONIC-R® or PLURADOT®.

Poloxamers are triblock copolymers with the structure PEO-PPO-PEO (where "PEO" is poly(ethylene oxide) and "PPO" is poly(propylene oxide). A considerable number of poloxamers is known, differing merely in the molecular weight and in the PEO/PPO ratio; Examples are poloxamer 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403 and 407. The poloxamers may be used in the process of the invention irrespective of their PEO/PPO ratio; for example, poloxamer 101 having a PEO/PPO weight ratio of about 10/90 and poloxamer 108 having a PEO/PPO weight ratio of about 80/20 both have been found to be valuable as non-crosslinkable polymer in the aqueous solution according to step a).

The order of polyoxyethylene and polyoxypropylene blocks can be reversed creating block copolymers with the structure PPO-PEO-PPO, which are known as PLURONIC-R® polymers.

Poloxamines are polymers with the structure $(PEO-PPO)_2$—N—$(CH_2)_2$—N—$(PPO-PEO)_2$ that are available with different molecular weights and PEO/PPO ratios. Again, the order of polyoxyethylene and polyoxypropylene blocks can be reversed creating block copolymers with the structure $(PPO-PEO)_2$—N—$(CH_2)_2$—N—$(PEO-PPO)_2$, which are known as TETRONIC-R® polymers.

Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available under the tradename PLURADOT®.

In a preferred embodiment, a guest material comprises a non-crosslinkable PVA which is free of ethylenically unsaturated groups and which has an average molecular weight $M_n$ being higher than that of the actinically-crosslinkable prepolymer for making a hydrogel lens of the invention. PVA is a highly biocompatible material used widely in ophthalmic products, especially wetting drops or artificial tears for ocular comfort (e.g., HypoTears™, etc.).

Non-crosslinkable PVAs of all kinds, for example those with low, medium or high polyvinyl acetate contents may be employed. In addition, the PVAs used may also comprise small proportions, for example up to 20%, preferably up to 5%, of copolymer units as mentioned before. The use of non-reactive PVAs with a contents of polyvinyl acetate units of less than 20%, preferably lower than 2%, is preferred.

The number-average molecular weight $M_n$ of the non-crosslinkable PVA is, for example, higher by at least 10000, preferably by at least 20000, than that of the actinically-crosslinkable prepolymer. For example, in the preferred case of a PVA prepolymer having an average molecular weight $M_n$ of from 12000 to 25000, the average molecular weight $M_n$ of the non-crosslinkable PVA is, for example, from 25000 to 100000, preferably from 30000 to 75000 and in particular from 35000 to 70000.

Preferably, a mixture of two or more different non-crosslinkable PVAs is added to the fluid prepolymer composition. The difference in average molecular weight $M_n$ between each of the non-crosslinkable PVAs is, for example, at least 10000. For example, in a preferred embodiment of the invention, the PVA prepolymer has an average molecular weight $M_n$ of from 12000 to 25000, and two non-crosslinkable PVAS, one having a lower average molecular weight $M_n$ of, for example, from 25000 to 50000, preferably from 30000 to 50000, and the other one having a higher average molecular weight $M_n$ of, for example, from above 50000 to 100000, preferably from above 50000 to 75000, are added.

In case of two or more different non-crosslinkable PVAs, the total amount thereof in the composition is as described before including the preferences given. The weight proportion of the lower molecular weight and higher molecular weight non-crosslinkable PVA may vary within broad ranges, but is, for example, from 1:1 to 5:1, preferably from 1:1 to 4:1, and in particular from 1:1 to 3:1.

The non-crosslinkable polyvinyl alcohols employed in the present invention are known and are commercially available, for example under the brand name Mowiol® from KSE (Kuraray Specialties Europe).

In another preferred embodiment, a guest material comprises a polyethyleneglycol (PEG) or a polyoxyethylene derivative.

In another preferred embodiment, a guest material comprises a mixture of non-crosslinkable PVAs and PEG. PVA and PEG may have synergy for enhancing surface wettability of a hydrogel contact lens. More preferably, the guest material further comprise a mucin-like material.

In accordance with the present invention, a packaging solution is ophthalmically compatible, meaning that a contact lens treated with the solution is generally suitable and safe for direct placement on the eye without rinsing, that is, the solution is safe and comfortable for contact with the eye via a contact lens that has been wetted with the solution. A packaging solution of the invention may be any water-based solution that is used for the storage of contact lenses. Typical solutions include, without limitation, saline solutions, other buffered solutions, and deionized water. The preferred aqueous solution is saline solution containing salts including one or more other ingredients known to a person skilled in the art. Examples of other ingredients include without limitation, suitable buffer agents, tonicity agents, water-soluble viscosity builders, surfactants, antibacterial agents, preservatives, and lubricants (e.g., cellulose derivatives, polyvinyl alcohol, polyvinyl pyrrolidone).

The pH of a packaging solution should be maintained within the range of about 6.0 to 8.0, preferably about 6.5 to 7.8. Examples of physiologically compatible buffer systems include, without limitation, acetates, phosphates, borates, citrates, nitrates, sulfates, tartrates, lactates, carbonates, bicarbonates, tris, tris derivatives, and mixtures thereof. The amount of each buffer agent is that amount necessary to be effective in achieving a pH of the composition of from 6.0 to 8.0.

Typically, the aqueous solutions for packaging and storing contact lenses are also adjusted with tonicity adjusting agents, to approximate the osmotic pressure of normal lacrimal fluids which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

Examples of suitable tonicity adjusting agents include, but are not limited to: sodium and potassium chloride, dextrose, glycerin, calcium and magnesium chloride. These agents are typically used individually in amounts ranging from about 0.01 to 2.5% (w/v) and preferably, form about 0.2 to about 1.5% (w/v). Preferably, the tonicity agent will be employed in an amount to provide a final osmotic value of 200 to 400 mOsm/kg and more preferably between about 250 to about 350 mOsm/kg, and most preferably between about 280 to about 320 mOsm/kg.

Examples of the preservative may be benzalkonium chloride and other quaternary ammonium preservative agents, phenylmercuric salts, sorbic acid, chlorobutanol, disodium edetate, thimerosal, methyl and propyl paraben, benzyl alcohol, and phenyl ethanol.

Surfactants can be virtually any ocularly acceptable surfactant including non-ionic, anionic, and amphoteric surfactants. Examples of preferred surfactants include without limitation poloxamers (e.g., Pluronic® F108, F88, F68, F68LF, F127, F87, F77, P85, P75, P104, and P84), poloamines (e.g., Tetronic® 707, 1107 and 1307, polyethylene glycol esters of fatty acids (e.g., Tween® 20, Tween® 80), polyoxyethylene or polyoxypropylene ethers of $C_{12}$-$C_{18}$ alkanes (e.g., Brij® 35), polyoxyethyene stearate (Myrj® 52), polyoxyethylene propylene glycol stearate (Atlas® G 2612), and amphoteric surfactants under the trade names Mirataine® and Miranol®.

A packaging solution preferably is an aqueous salt solutions that have an osmolarity of approximately from 200 to 450 milliosmol per 1000 ml (unit: mOsm/l), preferably an osmolarity of approximately from 250 to 350 mOsm/l, especially approximately 300 mOsm/l. A packaging solution can be a mixture of water or aqueous salt solution with a physiologically tolerable polar organic solvent, such as, for example, glycerol.

A hydrogel contact lens of the invention may be produced in a manner known per se, e.g. in a conventional "spin-casting mold", as described for example in U.S. Pat. No. 3,408,429, or by the so-called full cast-molding process in a static form, as described e.g. in U.S. Pat. Nos. 4,347,198, 5,508,317, 5,583,463, 5,789,464, and 5,849,810.

Lens molds for making contact lenses are well known to a person skilled in the art and, for example, are employed in cast molding or spin casting. For example, a mold (for full cast molding) generally comprises at least two mold sections (or portions) or mold halves, i.e. first and second mold halves. The first mold half defines a first molding (or optical) surface and the second mold half defines a second molding (or optical) surface. The first and second mold halves are configured to receive each other such that a lens forming cavity is formed between the first molding surface and the second molding surface. The molding surface of a mold half is the cavity-forming surface of the mold and in direct contact with a fluid prepolymer composition.

Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference.

Virtually all materials known in the art for making molds can be used to make molds for making contact lenses. For example, polymeric materials, such as polyethylene, polypropylene, polystyrene, PMMA, Topas® COC grade 8007-S10 (clear amorphous copolymer of ethylene and norbornene, from Ticona GmbH of Frankfurt, Germany and Summit, N.J.), or the like can be used. Other materials that allow UV light transmission could be used, such as quartz glass and sapphire.

In a preferred embodiment, where a fluid prepolymer composition is a solution, solvent-free liquid, or melt of one or more prepolymers optionally in presence of other components, reusable molds are used and the fluid prepolymer composition is cured actinically under a spatial limitation of actinic radiation to form a colored contact lens. Examples of preferred reusable molds are those disclosed in U.S. patent application Ser. No. 08/274,942 filed Jul. 14, 1994, Ser. No. 10/732,566 filed Dec. 10, 2003, Ser. No. 10/721,913 filed Nov. 25, 2003, and U.S. Pat. No. 6,627,124, which are incorporated by reference in their entireties.

In this case, the fluid prepolymer composition is put into a mold consisting of two mold halves, the two mold halves not touching each other but having a thin gap of annular design arranged between them. The gap is connected to the mold cavity, so that excess fluid prepolymer composition can flow away into the gap. Instead of polypropylene molds that can be used only once, it is possible for reusable quartz, glass, sapphire molds to be used, since, following the production of a lens, these molds can be cleaned rapidly and effectively off the uncrosslinked prepolymer and other residues, using water or a suitable solvent, and can be dried with air. Reusable molds can also be made of Topas® COC grade 8007-S10 (clear amorphous copolymer of ethylene and norbornene) from Ticona GmbH of Frankfurt, Germany and Summit, N.J. Because of the reusability of the mold halves, a relatively high outlay can be expended at the time of their production in order to obtain molds of extremely high precision and reproducibility. Since the mold halves do not touch each other in the region of the lens to be produced, i.e. the cavity or actual mold faces, damage as a result of contact is ruled out. This ensures a high service life of the molds, which, in particular, also ensures high reproducibility of the contact lenses to be produced.

The two opposite surfaces (anterior surface and posterior surface) of a contact lens are defined by the two molding surfaces while the edge is defined by the spatial limitation of actinic irradiation rather than by means of mold walls. Typically, only the fluid prepolymer composition within a region bound by the two molding surfaces and the projection of the well defined peripheral boundary of the spatial limitation is crosslinked whereas any fluid prepolymer composition outside of and immediately around the peripheral boundary of the spatial limitation is not crosslinked, and thereby the edge of the contact lens should be smooth and precise duplication of the dimension and geometry of the spatial limitation of actinic radiation. Such method of making contact lenses are described in U.S. patent application Ser. No. 08/274,942 filed Jul. 14, 1994, Ser. No. 10/732,566 filed Dec. 10, 2003, Ser. No. 10/721,913 filed Nov. 25, 2003, and U.S. Pat. No. 6,627,124, which are incorporated by reference in their entireties.

A spatial limitation of actinic radiation (or the spatial restriction of energy impingement) can be effected by masking for a mold that is at least partially impermeable to the particular form of energy used, as illustrated in U.S. patent application Ser. No. 08/274,942 filed Jul. 14, 1994 and U.S. Pat. No. 6,627,124 (herein incorporated by reference in their entireties) or by a mold that is highly permeable, at least at one side, to the energy form causing the crosslinking and that has mold parts being impermeable or of poor permeability to the energy, as illustrated in U.S. patent application Ser. No. 10/732,566 filed Dec. 10, 2003, Ser. No. 10/721,913 filed Nov. 25, 2003 and U.S. Pat. No. 6,627,124 (herein incorporated by reference in their entireties). The energy used for the crosslinking is radiation energy, especially UV radiation, gamma radiation, electron radiation or thermal radiation, the radiation energy preferably being in the form of a substantially parallel beam in order on the one hand to achieve good restriction and on the other hand efficient use of the energy.

Crosslinking may be initiated in the mold e.g. by means of actinic radiation, such as UV irradiation, ionizing radiation (e.g., gamma or X-ray irradiation).

What is notable is that the crosslinking according to the invention may be effected in a very short time, e.g. in ≤60 minutes, advantageously in ≤20 minutes, preferably in ≤10 minutes, most preferably in ≤5 minutes, particularly preferably in 1 to 60 seconds and most particularly in 1 to 30 seconds.

What is also notable is that the contact lenses according to the invention can be produced from a radiation-curable prepolymer in a very simple and efficient way compared with the prior art. This is based on many factors. On the one hand, the starting materials may be acquired or produced inexpensively. Secondly, there is the advantage that the prepolymers are surprisingly stable, so that they may undergo a high degree of purification. Therefore, for crosslinking, a polymer may be used which requires practically no more subsequent purification, such as in particular complicated extraction of unpolymerized constituents. Furthermore, crosslinking may take place solvent-free or in aqueous solution, so that a subsequent solvent exchange or the hydration step is not necessary. Finally, photo-polymerization is effected within a short period, so that from this point of view also the production process for the contact lenses according to the invention may be set up in an extremely economic way.

Opening of the mold so that the molded article can be removed from the mold may take place in a manner known per se.

If the molded contact lens is produced solvent-free from an already purified prepolymer according to the invention, then after removal of the molded lens, it is not normally necessary to follow up with purification steps such as extraction. This is because the prepolymers employed do not contain any undesired constituents of low molecular weight; consequently, the crosslinked product is also free or substantially free from such constituents and subsequent extraction can be dispensed with. Accordingly, the contact lens can be directly transformed in the usual way, by hydration, into a ready-to-use contact lens. Appropriate embodiments of hydration are known to the person skilled in the art, whereby ready-to-use contact lenses with very varied water content may be obtained. The contact lens is expanded, for example, in water, in an aqueous salt solution, especially an aqueous salt solution having an osmolarity of about 200 to 450 milli-osmole in 1000 ml (unit: mOsm/ml), preferably about 250 to 350 mOsm/l and especially about 300 mOsm/l, or in a mixture of water or an aqueous salt solution with a physiologically compatible polar organic solvent, e.g. glycerol. Preference is given to expansions of the article in water or in aqueous salt solutions.

If the molded contact lens is produced from an aqueous solution of an already purified prepolymer according to the invention, then the crosslinked product also does not contain any troublesome impurities. It is therefore not necessary to carry out subsequent extraction. Since crosslinking is carried out in an essentially aqueous solution, it is additionally unnecessary to carry out subsequent hydration. The contact lenses obtained by this process are therefore notable, according to an advantageous embodiment, for the fact that they are suitable for their intended usage without extraction. By intended usage is understood, in this context, that the contact lenses can be used in the human eye.

In a preferred embodiment, a soft hydrogel contact lens has a permeability-control coating capable of control diffusion rate of a guest material out of the lens. Alternatively, a soft hydrogel contact lens has an asymmetrical coating composed of an anterior surface coating and a posterior coating, wherein the anterior and posterior surface coatings have different permeability for a guest material. Such coatings can be prepared as described in U.S. Pat. No. 6,811,805 (herein incorporated by reference in its entirety).

The present invention, in another aspect, provides a process for making a soft contact lens capable of gradually delivering a guest material over an extended period of wearing time. The method of the invention comprises the steps of: a) obtaining a fluid prepolymer composition comprising an actinically-crosslinkable prepolymer and a guest material, wherein the actinically-crosslinkable prepolymer comprises ethylenically unsaturated groups and can be polymerized thermally or actinically to form the polymer matrix of the soft contact lens, wherein the guest material is free of any groups capable of being thermally or actinically crosslinked with the actinically-crosslinkable prepolymer, wherein the guest material is present in an amount sufficient to provide a desired functionality to the soft contact lens; b) introducing an amount of the fluid prepolymer composition in a mold for making a contact lens; c) polymerizing the actinically-crosslinkable prepolymer in the mold to form the soft contact lens with the guest material being not covalently linked to the polymer matrix but being distributed therein in a substantially uniform manner; d) packaging the resultant soft contact lens in a container containing a packaging solution; and e) sterilizing the soft contact lens in the package, wherein the sterilized soft contact lens is capable of gradually releasing the guest material during wear over at least about 6 hours, provided that the method is free of any extraction step.

Any containers can be used in the invention. Examples of contact lens containers are blister packages with various form as well known to a person skilled in the art.

Contact lenses can be sterilized by autoclaving them in a manner known per se after their removal from the molds.

The process according to the invention is outstandingly well suited to the economical manufacture of a large number of moldings, such as contact lenses, in a short time. The contact lenses obtained in accordance with the process according to the invention have inter alia the advantages over the contact lenses known from the state of the art that they can be used for their intended use without subsequent treatment steps, such as extraction or hydration.

The contact lenses according to the invention can be produced in a very simple and efficient manner compared with the state of the art. This is as a result of several factors. First, the starting materials can be obtained or produced at a favorable cost. Secondly, there is the advantage that the prepolymers are stable, so that they can be subjected to a high degree of purification. It is therefore possible to use for the crosslinking a prepolymer that requires practically no subsequent purification, such as especially a complicated extraction of unpolymerized constituents. Also, the polymerization can be carried out in aqueous solution, so that a subsequent hydration step is not necessary. Without extraction and hydration, a guest material may not be lost during purification processes subsequent to cast-molding. The photopolymerization occurs within a short period, so that the process for manufacturing the contact lenses according to the invention can be organized to be extremely economical from that point of view also.

All of the advantages mentioned above naturally apply not only to contact lenses but also to other moldings according to the invention. Taking into account all the various advantageous aspects in the manufacture of the moldings according to the invention it can be seen that the moldings according to the invention are especially suitable as mass-produced articles, such as, for example, contact lenses that are worn for a short time and then replaced by new lenses and that is capable of delivering a drug or a lubricant in a time-controlled manner.

The present invention, in a further aspect, provides a method for time-controlled delivery of a drug or a lubricant. The method of the invention comprises the steps of: a) obtaining a sealed package which include a packaging solution and a soft hydrogel contact lens which is obtained by cast-molding of a polymerizable composition in a mold, wherein the fluid polymerizable composition comprises a drug or lubricant without ethylenically unsaturated groups and at least one polymerizable component from the group consisting of a vinylic monomer, a macromer with one or more ethylenically unsaturated groups, an actinically-crosslinkable prepolymer with ethylenically unsaturated groups, and combinations thereof, wherein the polymer matrix of the contact lens is formed from thermal or actinic polymerization of ethylenically unsaturated groups in the polymerizable component, wherein the drug or lubricant is not covalently linked to the polymer matrix but being distributed therein, wherein the drug or lubricant is present in an amount sufficient to provide a desired functionality to the contact lens, and wherein the drug or lubricant is characterized by a ratio of eye blink-activated diffusion to passive diffusion being about 1.5 or greater; b) wearing the soft hydrogel contact lens in an eye; and c) gradually delivering, under eye blinks, the drug or lubricant during wear over at least about 6 hours.

Preferably, the polymerizable composition is a prepolymer composition comprising an actinically-crosslinkable prepolymer and the soft hydrogel contact lens is produced in a manufacturing process without any extraction steps.

Ratio of eye blink-activated diffusion to passive diffusion is preferably about 2.5 or greater, more preferably about 4.0 or greater, even more preferably about 6.0 or greater.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

Example 1

Fluid prepolymer compositions (aqueous formulations) are prepared from nelfilcon A (an acrylated-poly(vinyl alchohol) which is water-soluble and actinically-crosslinkable, from CIBA Vision), water, photoinitiator (Irgacure 2959; Ciba Specialty Chemicals), 4-hydroxy-2,2,6,6-tetramethylpiperpiperindinyloxy, free radical (HO-TEMPO; Aldrich Chemicals), poloxamer 108 (Pluronics® F38), non-crosslinkable PVAs (Mowiol 6-98 having Mw~47000 from KSE and Mowiol 10-98 having Mw~61000 from KSE), and copper phthalocyanine (CuP). Control Formulation. A control formulation is prepared to contain 30% by weight of nelfilcon A, 0.1% by weight of Irgacure 2959, 0.3% by weight of poloxamer 108, and 47 ppm TEMPO. Formulation I. Formulation I is prepared by adding 1% (wt/col) of Mowiol 6-98 and 0.5% Mowiol 10-98 (in a proportion of 3 Mowiol 6-98 to 1 Mowiol 10-98) in the control formulation. Formulation II. Formulation II is prepared from control formulation by adding 1% (wt/col) of Mowiol 6-98 and 0.5% Mowiol 10-98 (in a proportion of 3 Mowiol 6-98 to 1 Mowiol 10-98) and 45 ppm CuP in the control formulation.

Example 2

Lens Production

A formulation prepared in Example 1 is dispensed onto a female mold half by using an EFD automatic dispenser (4 bar, 1.2 sec). The female mold half is then mated with a corresponding male mold half. The mold is closed by using a pneumatic closing system. The formulation is UV cured under 2 different UV lights (1.8 mW/cm$^2$ each) for total exposure time of 4.9 sec.

Each lens is packaged in a conventional blister package containing 0.85 ml phosphate buffered saline and sealed with an aluminum sealing foil. Each lens is autoclaved in the package at 122° C. After autoclaving, the diameter and the E-modulus of the contact lenses are determined. No significant differences in lens diameter and mechanical properties (modulus, elongation, stress, and toughness at break) can be identified between lenses made from the control formulation and formulations I and II.

Example 3

Tests are conducted to evaluate the chemical and physical profile of contact lenses produced in Example 2 under both ambient and accelerated conditions (at 45° C.). For ambient conditions, samples are stored and test at 25° C. at baseline. For accelerated conditions, samples are stored and test at 45°±° C. at 3 and 9 months (equivalent to 12 and 36 months storage at ambient temperature respectively). The stability study follows the guidelines outlined in ISO 11987 for chemical and physical testing required in order to determine the stability of contact lenses and to determine shelf life for these lenses in the blister foil package. There is no significant change in pH and osmolarity of the package saline, light transmittance and percent water content of the lens, power, diameter, and base curve, modulus.

Example 4

This example illustrates studies of extraction of non-crosslinkable PVAs from contact lenses produced in Example 2, using Gel Filtration Chromatographic Analysis (GFC). All tested lenses have been stored in the package for about 3 days before testing. The leachable PVA is measured in phosphate buffered lens extracts (100 lenses/5 ml phosphate buffered saline held at 35° C. to approximate ocular temperature) obtained at a series of sampling times (at 4, 8, 12, 16, and 24 hours of extraction times). PVA leachables in the package saline is also measured. The molecular weight of the PVA in the leachables is measured using gei filtration chromatography with refractive index (RI) detection. The molecular weight averages are determined relative to broad PVA molecular weight standards. Because the PVA in the leachables does not have exactly the same MW distribution as any of the PVA added to the formulation, a direct measurement of the concentration is not possible. The approximate PVA concentration from the samples is calculated using their peak areas vs. those for standards of Mowiol 6-98 and Mowiol 10-98 PVA on a single standard curve.

Package Saline:

Package saline is collected from 10-30 lens packages from each group and pooled. Analysis of the PVA in the saline is performed without any further sample dilution.

Phosphate Buffered Saline:

Saline containing 0.025 M $KH_2PO_4$ and 0.025 M $Na_2HPO_4$ is adjusted to pH=7 using NaOH.

Phosphate Buffered Lens Extracts:

For each time point, 100 lenses from each group is removed from packages, blotted dried, and placed in a scintillation vial. Five (5) ml of phosphate buffered saline is added. Samples are placed in a water bath during the extraction period. At each time point, the phosphate buffered lens extract is removed and stored for analysis.

PVA Molecular Weight Standards:

Broad molecular weight standards with $M_w$ values ranging from 6,000 to 162,000 is from Polymer Standard Service (0.1-0.2% w/v in UP water).

PVA Concentration Standard Preparation:

Stock standards of each of Mowiol 6-98 and Mowiol 10-98 is prepared from ultrapure water at a nominal concentration of 0.1 g/100 ml UP water. To dissolve the PVA, it is necessary to heat the samples for about 1 hour at about 90° C. From the stocks, working standards of 500, 100, and 50 ppm are made.

GFC System:

Mobil phase—0.10 M $NaNO_3$/10% CAN

Column—Waters Ultrahydrogel 250+Ultrahydrogel linear with UH guard column

Pump Flow—1.0 ml/min

Injection Volume—160 μl

Run Time—65 minutes

RI Detector—Sensitivity 128, Internal Temperature 45° C.

It is found that high molecular weight leachable (elutable) PVA is only detected in package salines containing contact lenses made from Formulation I or II. No high molecular weight elutable PVA is detected in package salines containing control contact lenses made from the Control Formulation.

FIG. 1 shows results of PVA leachables determined from the above experiments. It clearly indicates that with addition of Mowiol 6-98 and Mowiol 10-98 in the lens formulation, a much greater amount of PVA can be released from each lens over up to 24 hours.

Example 5

This example illustrates a series of in vitro experiments to mimic in vivo eye blink-activated PVA release from a lens into the tear layer.

Assay of PVA Leachables.

The assay is based on measurements of Refractive index (RI). A highly sensitive microrefractometer (Index Instruments Automatic GPR 11-37) is used in the experiments. The RI of a series of PVA standards of different molecular weights is measured at 25° C. in the isotonic phosphate buffered saline that is used as packaging solution. The relationship between refractive index and concentration is linear, and not dependent upon molecular weight of PVA in the range used in the fabrication of contact lenses (Example 2).

Experiment Design.

A contact lens is first blotted dry and immediately is carefully placed into 100 μl of an extraction medium in an Eppendorf microtube and the microtube is agitated for fifteen second. At the end of one hour period, the tube is agitated using, e.g., a Vibrex vortex mixer, for a further fifteen seconds. The extraction medium is removed from the Eppendorf microtube and 100 μl of a fresh extraction medium is added. Extraction samples are stored at 25° C. between agitation procedures. The concentration of a guest material extracted out of a lens can be determined according to any methods known to a person skilled in the art. Cumulative concentration can be calculated from consecutive extractions.

Figure 2:
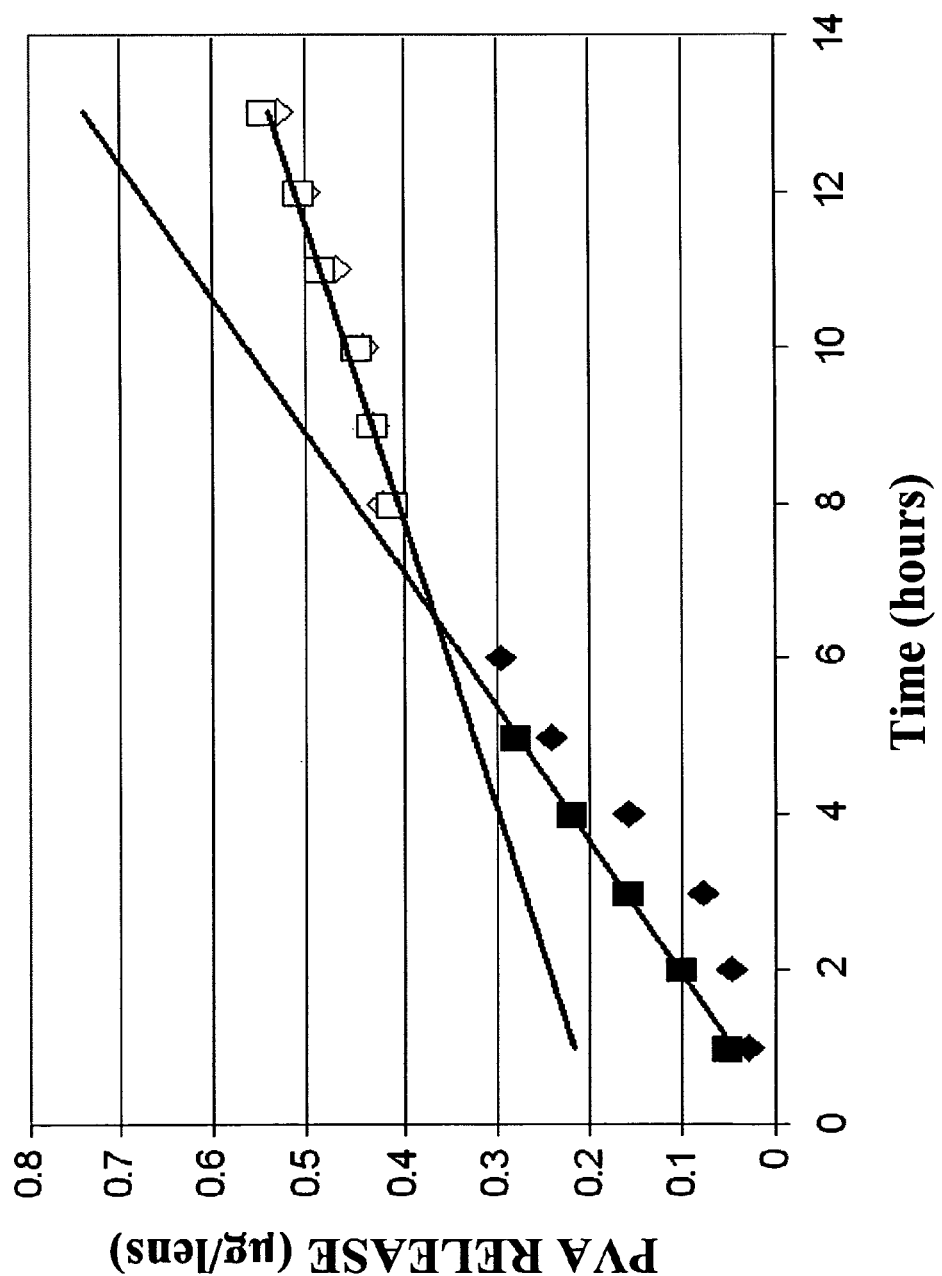
FIG. 2 shows in vitro PVA extraction from fresh contact lenses (solid symbols) and worn contact lenses (open symbols).

Contact lenses made from Formulation I (represented by rectangular symbols) or Formulation II (represented by diamond symbols) in Example 2 are tested as follows. Fresh lenses (i.e., unworn lens) are tested according to the in vitro experiment procedures described above. Worn lenses, which have been worn for 6 hours, are also tested according to the in vitro experiment procedures described above. Results are shown in FIG. 2 and demonstrate that there is a correlation between the in vitro and in vivo PVA release.

Example 6

This example illustrates a series of in vitro experiments to study PVA release profile of contact lenses (made in Example 2) after 9 month storage at 45° C.

Lenses having power of −1.00D, −1.25D, and −1.50D are used in the studies. Triplicate measurements are performed for lenses with each power according to the experiment procedures described in Example 5 (in vitro experiments to mimic in vivo eye blink-activated PVA release from a lens into the tear layer). Experiment data show that the overall release profiles of all lenses made from Formulations I and II are similar. PVA release patterns are consistent with those observed in the experiments performed shortly after lens production.

Example 7

This example illustrates a series of comparative studies of passive diffusion, eye blink-activated diffusion (vortexted), and thermally enhanced diffusion.

Contact lenses (Rx=−2.50 D) are prepared according to the procedure described in Example 2.

Assay of PVA leachables is based on measurements of Refractive index (RI) as described in Example 5.

Passive diffusion as function of cumulative extraction time is carried out at 25° C. as follows. A contact lens is first blotted dry and immediately is carefully placed into 100 μl of an extraction medium (water or saline or buffered saline) in an tube (e.g., a centrifuge tube, a scintillation vial, or preferably an Eppendorf microtube). Each extraction lasts about one hour and maintained at room temperature (e.g., 25° C.) without agitation. The extraction medium is removed from the Eppendorf microtube after each extraction and 100 μl of a fresh extraction medium is added. The concentration of the PVA leachables PVA in each extraction medium is determined by measurements of refractive index (RI). Cumulative concentrations are calculated from consecutive passive extractions.

Thermally enhanced diffusion as function of cumulative extraction time is carried out at 34° C. as follows. A contact lens is first blotted dry and immediately is carefully placed into 100 μl of an extraction medium (water or saline or buffered saline) in an tube (e.g., a centrifuge tube, a scintillation vial, or preferably an Eppendorf microtube). Each extraction lasts about one hour and maintained at 34° C. without agitation. The extraction medium is removed from the Eppendorf microtube after each extraction and 100 μl of a fresh extraction medium is added for the next extraction. The concentration of the PVA leachables PVA in each extraction medium is determined by measurements of refractive index (RI). Cumulative concentrations are calculated from consecutive thermally enhanced extractions.

Eye blink-activated diffusion as function of cumulative extraction time is determined according to the procedure described in Example 5. A contact lens is first blotted dry and immediately is carefully placed into 100 μl of an extraction medium in an Eppendorf microtube and the microtube is agitated for fifteen second. At the end of one hour period, the tube is agitated using, e.g., a Vibrex vortex mixer, for a further fifteen seconds. The extraction medium is removed from the Eppendorf microtube and 100 μl of a fresh extraction medium is added for the next vortexted extraction. Extraction samples are stored at 25° C. between agitation procedures. The concentration of the PVA leachables PVA in each extraction medium is determined by measurements of refractive index (RI). Cumulative concentrations are calculated from consecutive vortexted extractions.

Figure 3:
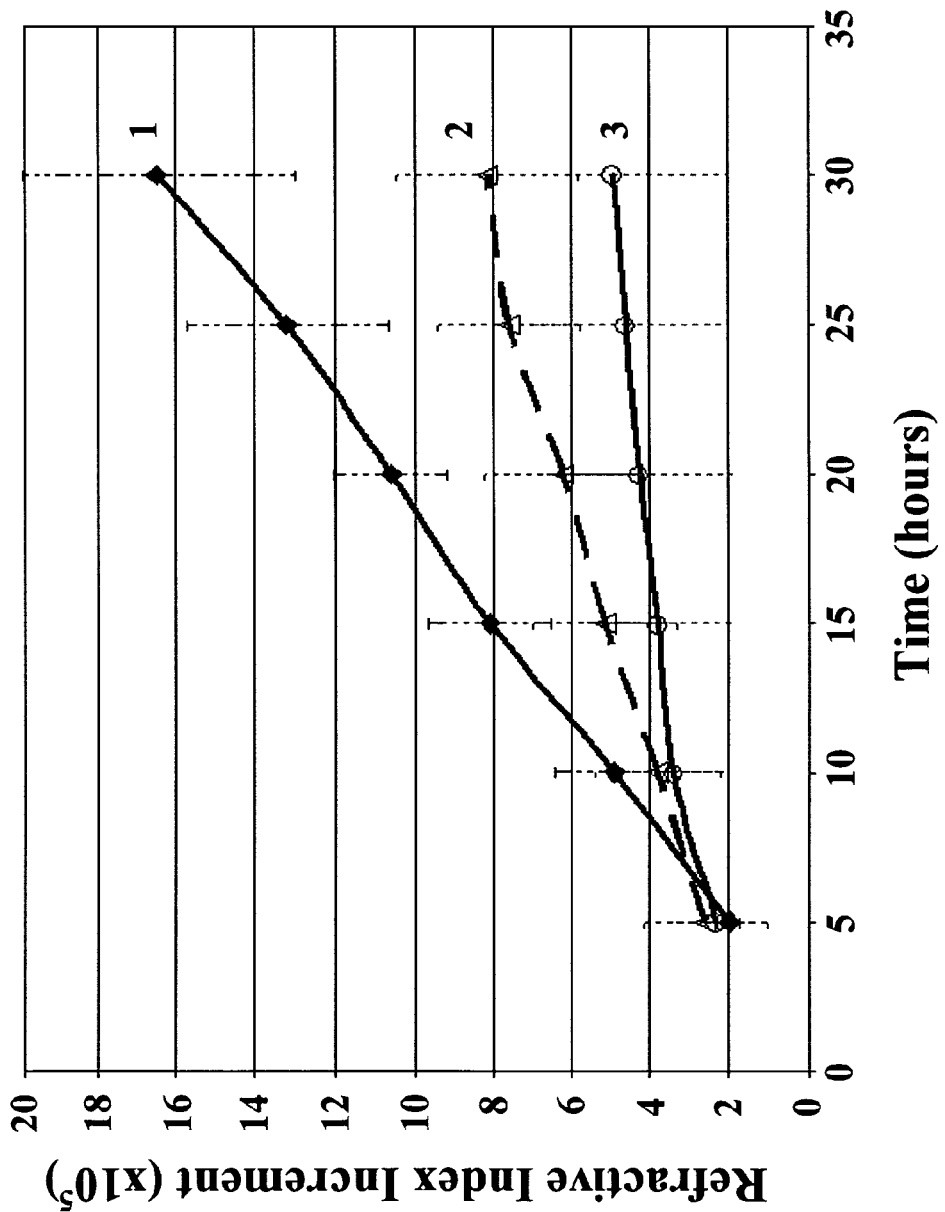
FIG. 3 illustrates that vortexted diffusion (eye blink-activated diffusion) (curve 1) and thermally enhanced diffusion (curve 2, passive diffusion at about 34° C.) is faster than passive diffusion (curve 1).

Triplicate measurements are performed for each experiment. Results are shown in FIG. 3, which clearly indicates that vortexted diffusion (eye blink-activated diffusion) and thermally enhanced diffusion is faster than passive diffusion. This result supports the hypothesis in which under eye blinks and/or thermal conditions (34° C.), leachable PVAs can leach out of a contact lens of the invention.

Ratios of eye blink-activated diffusion (vortexted diffusion) to passive diffusion at different cumulative extraction times are reported in Table 1.

TABLE 1

|  | Cumulative Extraction Time (hours) | | | | | |
| --- | --- | --- | --- | --- | --- | --- |
|  | 1 | 2 | 3 | 4 | 5 | 6 |
| Vortexted diffusion | 0.9 | 1.4 | 2.1 | 2.5 | 2.9 | 3.3 |
| Passive diffusion | | | | | | |

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

The invention claimed is:

1. An ophthalmic product, comprising:
a sealed package including a packaging solution and a soft hydrogel contact lens, wherein the hydrogel contact lens comprises a polymer matrix and a guest material which is not covalently linked to the polymer matrix but distributed therein,
wherein the hydrogel contact lens has a capability of gradually releasing the guest material during wear over at least about 6 hours after storing in the packaging solution for at least about one month,
wherein the hydrogel contact lens is produced by cast-molding in a mold of a fluid prepolymer composition without being subjected to any extraction processes,
wherein the prepolymer composition comprises the guest material and an actinically-crosslinkable prepolymer from which the polymer matrix is formed by polymerization,
wherein the guest material comprises a drug which is free of any groups capable of being actinically crosslinked with the actinically-crosslinkable prepolymer and present in an amount sufficient to be released from the contact lens over at least about 6 hours of wearing time,
wherein the actinically-crosslinkable prepolymer is a polyhydroxyl compound having a molecular weight of at least about 2000 and comprising from about 0.5 to about 80%, based on the number of hydroxyl groups in the poly(vinyl alcohol), of units of the formula I, and II, I and III, or I and II and III

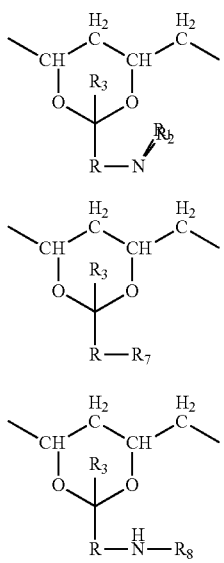

in which
the molecular weight refers to a weight average molecular weight, Mw, determined by gel permeation chromatography,
R is linear or branched alkylene having up to 12 carbon atoms,
$R_1$ is hydrogen or lower alkyl having up to seven carbon atoms,
$R_2$ is an ethylenically unsaturated, electron-withdrawing, crosslinkable radical having up to 25 carbon atoms,
$R_3$ is hydrogen, a $C_1$-$C_6$ alkyl group or a cycloalkyl group,
$R_7$ is a primary, secondary, tertiary amino group, or a quaternary amino group of the formula $N^+(R')_3 X^-$, in which each R', independently of the others, is hydrogen or a $C_1$-$C_4$ alkyl radical and X is a counterion,
$R_8$ is the radical of a monobasic, dibasic or tribasic, saturated or unsaturated, aliphatic or aromatic organic acid or sulfonic acid.

2. The ophthalmic product of claim 1, wherein the fluid prepolymer composition is an aqueous solution, wherein the actinically-crosslinkable prepolymer is water soluble.

3. The ophthalmic product of claim 1, wherein the actinically-crosslinkable prepolymer is a water-soluble prepolymer selected from the group consisting of: a water-soluble crosslinkable poly(vinyl alcohol) prepolymer; a water-soluble vinyl group-terminated polyurethane; derivatives of a polyvinyl alcohol, polyethyleneimine or polyvinylamine; a water-soluble crosslinkable polyurea prepolymer; crosslinkable polyacrylamide; crosslinkable statistical copolymers of vinyl lactam, methyl methacrylate and a comonomer; crosslinkable copolymers of vinyl lactam, vinyl acetate and vinyl alcohol; polyether-polyester copolymers with crosslinkable side chains; branched polyalkylene glycol-urethane prepolymers; polyalkylene glycol-tetra(meth)acrylate prepolymers; crosslinkable polyallylamine gluconolactone prepolymers, and mixtures thereof.

4. The ophthalmic product of claim 1, wherein the actinically-crosslinkable prepolymer is a silicone-containing prepolymer.

5. The ophthalmic product of claim 1, wherein the guest material has a kinetically-unfavorable passive diffusion out of the contact lens, characterized by a ratio of eye blink-activated diffusion to passive diffusion being about 1.6 or greater, determined after a cumulative extraction period of at least about 3 hours.

6. The ophthalmic product of claim 5, wherein the ratio of eye blink-activated diffusion to passive diffusion is about 2.4 or greater, determined after a cumulative extraction period of at least about 4 hours.

7. The ophthalmic product of claim 5, wherein the guest material comprises a mucin-like material, an ophthalmically beneficial material, or a mixture thereof, wherein the mucin-like material is polyglycolic acid, polylactide, collagen, gelatin, or a mixture thereof, wherein the ophthalmically-beneficial material is 2-pyrrolidone-5-carboxylic acid (PCA) or salt thereof, an amino acid or salt thereof, an alpha hydroxyl acid or salt thereof, a linoleic acid or salt thereof, a gamma linoleic acid or salt thereof, a vitamin, or a mixture thereof.

8. The ophthalmic product of claim 1, wherein the soft hydrogel contact lens has a permeability-control coating capable of controlling the diffusion rate of the guest material out of the soft hydrogel contact lens.

9. The ophthalmic product of claim 1, wherein the soft hydrogel contact lens has an asymmetrical coating composed of an anterior surface coating and a posterior coating, wherein the anterior and posterior surface coatings have a different permeability for the guest material.

* * * * *